ically interlocked by pulling the later rearwards in use of the tampon.

United States Patent [19]

Suzuki et al.

[11] Patent Number: 4,921,474
[45] Date of Patent: May 1, 1990

[54] SANITARY TAMPON APPLICATOR

[75] Inventors: Migaku Suzuki; Yamamoto Masamitsu, both of Kawanoe, Japan

[73] Assignee: Uni-Charm Corporation, Ehime, Japan

[21] Appl. No.: 259,895

[22] Filed: Oct. 19, 1988

Related U.S. Application Data

[63] Continuation of Ser. No. 163,803, Mar. 3, 1988, abandoned, which is a continuation of Ser. No. 919,100, Oct. 15, 1986, abandoned.

[30] Foreign Application Priority Data

Oct. 18, 1985 [JP] Japan .................................. 60-234283

[51] Int. Cl.$^5$ ............................................. A61F 13/20
[52] U.S. Cl. ......................................... 604/16; 604/18
[58] Field of Search ..................................... 604/14–18, 604/904

[56] References Cited

U.S. PATENT DOCUMENTS 3,749,094  7/1973  Duncan ................................. 604/15
4,048,998  9/1977  Nigro ................................... 604/14
4,411,647 10/1983  Sakurai et al. ........................ 604/16

Primary Examiner—C. Fred Rosenbaum
Assistant Examiner—Sharon Rose
Attorney, Agent, or Firm—Fred Philpitt

[57] ABSTRACT

A sanitary tampon applicator comprises an outer sleeve to accommodate a tampon and an inner sleeve slidably telescoped into the outer sleeve to extrude the tampon through a front open end of the outer sleeve, the inner sleeve comprising a first inner sleeve member and a second inner sleeve member slidably inserted into the former and a rear end of the former and a front end of the latter are automatically interlocked by pulling the later rearwards in use of the tampon.

9 Claims, 5 Drawing Sheets

SANITARY TAMPON APPLICATOR

This is a continuation of Ser. No. 163,803, filed Mar. 3, 1988, now abandoned, which in turn of continuation of application Ser. No. 919,100, filed 10/15/86, now abandoned.

BACKGROUND OF THE INVENTION

The present invention relates to applicator used to insert a tampon into vagina, thereby to absorb menstrual blood and to clog said vagina.

As the applicator for this purpose, there has already been used in practice the construction comprising a plastic outer sleeve adapted to accommodate therein a tampon and a plastic inner sleeve slidably telescoped into the outer sleeve so as to extrude the tampon through a front open end of the outer sleeve. However, such applicator of well known art tends to be bulky in its length and inconvenient for packaging as well as for being carried with user.

To overcome such inconvenience, the improved applicator has been proposed, as disclosed by Japanese Utility Model Publication No. 59-9621 and Japanese Patent Publication No. 60-27303, in which the inner sleeve comprises a first inner sleeve member and a second inner sleeve member slidably telescoped into the first inner sleeve member, and a rear end of the first inner sleeve member and a front end of the second inner sleeve member being provided with stoppers so that these rear and front ends are automatically interlocked by pulling the second inner sleeve member rearwards in use of a tampon.

The applicator disclosed by Utility Model Publication No. 59-9621 is shown by FIGS. 8 and 9. FIG. 8 is a fragmentary section illustrating the applicator of prior art as a first inner sleeve member and a second inner sleeve member constituting together the inner sleeve are not interlocked, and FIG. 9 is a view similar to FIG. 6 but illustrating the applicator as said sleeve members are interlocked. A plastic inner sleeve 2 slidably telescoped into a plastic outer sleeve 1 comprises a first inner sleeve member 3 and a second inner sleeve member 4 slidably inserted into the first inner sleeve member 3. The first inner sleeve member 3 is provided adjacent and at the rear end with projections 5 formed by partially cutting and bending inwards the material and the annular projection 6 directed radially inwards, respectively, while the second inner sleeve member 4 is provided at its front end with the annular projection 7 circumferentially extending around the outer periphery thereof so that the annular projection 7 may ride across said projection 5 against elasticity thereof and be interposed between the projections 5 and the annular projection 6 when the second inner sleeve member 4 has been completely pulled rearwards.

The variant of this well known construction is illustrated by FIGS. 10 and 11 corresponding to FIGS. 8 and 9, respectively. This variant is basically similar to the construction as illustrated by FIGS. 8 and 9 except that the first inner sleeve member 3 is gradually diameter-reduced rearwards and provided on the inner periphery at its rear end with the annular groove 8 while the second inner sleeve member is provided on the outer periphery at its front end with the annular projection 9 adapted to be engaged in said annular groove 8 when the second inner sleeve member 4 has been completely pulled rearwards.

The applicator disclosed by Patent Publication No. 60-27303 is shown in FIGS. 12 and 13 corresponding to FIGS. 8 and 9. The applicator is fundamentally similar to those as illustrated in FIGS. 8 through 11, as will be apparent from FIGS. 12 and 13, except that a second inner sleeve member 4 is provided on the outer periphery of its front end with projection 11 and, with a spacing axially behind the projection 11, non-annular projections 12 diametrically opposed to each other and directed towards the projection 11 while the first inner sleeve member 3 is provided on the inner periphery at its rear end with the projection 13 adapted to be interposed between the projection 11 and the non-annular projections 12 when the second inner sleeve member 4 has been pulled rearwards.

Referring to these figures, reference numeral 15 designates the conventional tampon including the pull-chord 16.

In such applicator, it has been general in practice that the outer sleeve 1 is formed as a cylindrical piece having a relatively small diameter, for example, of 10 to 13 mm so as to be inserted into vagina without any damage of vaginal membrane and the tampon 15 accommodated in this outer sleeve is formed as a round rod by compressing relatively bulky absorbent so that the outer periphery of the tampon may be in close contact with the inner periphery of the outer sleeve 1 when inserted thereinto in view of requirement that the tampon should absorb menstrual blood as plenty as possible and effectively clog vagina by swelling. Accordingly, the inner sleeve 2 is encountered by a certain degree of resistance when the tampon is extruded by the inner sleeve 2 through the front end of the outer sleeve 1. Such resistance is further enhanced by a pressure necessary to spread the petal-like segments normally closing the front end of the outer sleeve 1. It should be understood that these petal-like segments are measures to facilitate insertion of the outer sleeve 1 into the opening of vagina and employed by the previously mentioned applicators of the prior arts. Furthermore, depending upon the posture taken by user during inserting the tampon into vagina, the tampon may strike against vagina wall and cause a resistance. In any cases, the inner sleeve 2 is encountered by more or less resistance during a period from inserting the tampon through the opening of vagina to final positioning it into the desired location within vagina by extruding operation of said inner sleeve. It is important, therefore, that the interlocking effect to be established between the first inner sleeve member 3 and the second inner sleeve member 4 constituting together the inner sleeve 2 should be sufficiently stable to overcome said resistance.

The outer sleeve 1 of a relatively small diameter should be molded from material as soft as possible and correspondingly requiring adequate strength and thickness because the outer sleeve 1 is destined to be inserted into vagina. As it will be obvious, the first inner sleeve member 3 should be of a diameter sufficiently small to be inserted into the outer sleeve 1 and the second inner sleeve member 4 should be of a diameter sufficiently small to be inserted into the first inner sleeve member 3. The inner diameter of the second inner sleeve member 4 must be adequate to enable the pull-chord to pass therethrough. With a consequence, the first inner sleeve member 3, the second inner sleeve member 4, the projections 5, 12 and others should necessarily have relatively small thicknesses. It is practically difficult, for the reason of said requirements, to mold the first inner sleeve member 3 and the second inner sleeve member 4 of thicknesses larger than approximately 1 mm from synthetic resin. (1) With the applicator as illustrated by FIGS. 8 and 9, it is practically difficult to mold the interlocked portions of the first inner sleeve member 3 and the second inner sleeve member 4 which are subject to said resistance during insertion of the tampon, particularly the non-annular projections 5 destined to be directly subject to the pressure of the annular projection 6 with a thickness larger than approximately 1 mm, so the non-annular projections 5 may sometimes be bent or broken in the direction of said pressure, making operation of tampon extrusion impossible.

Also with the variant disclosed by FIGS. 10 and 11, the annular projection 9 is certainly engaged in the annular groove 8 against the elasticity of the first inner sleeve member 3, but this engagement is never stable and the annular projection 9 may be easily disengaged from the annular groove 8, making said operation of tampon extrusion impossible, because said engagement is easily established.

The applicator illustrated by FIGS. 12 and 13 is accompanied with, in addition to the above-mentioned problem, further problems as will be described below. In non-use, i.e., in the state that the second inner sleeve member 4 is still not pulled rearwards, the non-annular projections 12 remains yielding to a pressure exerted by the inner side of the first inner sleeve member 3 against the spring of the non-annular projections 12 themselves. Even when it is assumed that the second inner sleeve member 4 (inclusive of the non-annular projections 12) has been molded from synthetic resin of relatively high elasticity, said condition of yielding to the pressure lasting for a relatively long period may cause a fatigue in the non-annular projections 12 and, in consequence, said yielding may be fixed, so that the non-annular projections 12 may not restore their initial positions and, as a result, may not be engaged with the projection 13. There often elapse several months from the date of fabrication of the tampon to the actual use thereof by user, and this problem of fatigue is serious in view of this fact. Even if said engagement has been achieved, the pressure of the non-annular projections 12 exerted on the projection 13 may possibly lift the non-annular projections 12 in the direction opposed to the direction in which the pressure of the second inner sleeve member 4 is exerted, resulting in that the tips of the non-annular projections 12 protrude above the outer periphery of the first inner sleeve member 3 and the second inner sleeve member 4 can not be inserted into the outer sleeve 1.

In this manner, said applicators of the prior arts are far from the desired condition that the interlocking effect between the first inner sleeve member 3 and the second inner sleeve member 4 is reliable and stable sufficiently to overcome said resistance.

(2) Concerning the operation of tampon extrusion, the inner sleeve 2 is necessarily subject to more or less resistance as has been previously mentioned, this operation become difficult when the diameter of the inner sleeve 2 and particularly of its rear open end against which user's finger bears is small. Such inconvenience is further serious for the inner sleeve 2 consisting of the first inner sleeve member 3 and the second inner sleeve member 4 slidably telescoped into the first inner sleeve member 3 than for the inner sleeve 2 consisting of the single member, but none of the well known applicators has employed a measure to solve this problem. Certainly, the second inner sleeve member 4 is provided on the outer periphery of its rear end with the reinforcing annular rib, as seen from FIGS. 8 through 13, but the diameter of such annular rib can not solve said problem.

(3) With the above-mentioned applicators of the prior arts, as will be understood from FIGS. 8, 10 and 12, the second inner sleeve member 4 is not engaged with the first inner sleeve member 3 and the second inner sleeve member 4 easily displaces within the first inner sleeve member 3 in the axial direction even after assembly of the applicator and charging of the tampon into the outer sleeve 1 have been completed. Such displacement of the second inner sleeve member 4 disturbs operation of individually packaging the applicators.

OBJECT OF THE INVENTION

Object of the present invention is to provide an improved tampon applicator having the construction similar to said applicators but free from said problems (1) through (3).

According to the applicator of the present invention is so constructed that, when the tampon is not in use, the first inner sleeve member and the second inner sleeve member constituting together the inner sleeve serving to extrude the tampon are provisionally engaged with each other so as to prevent the second inner sleeve member from axial displacement within the first inner sleeve member, facilitating the applicators to be individually packaged. The projections provided on the second inner sleeve member are stationary (fixed) and this feature is advantageous in that the problems encountered by the applicators of the prior arts in which the corresponding projections are radially deformable, i.e., unstable, or ineffective interlocking between the rear end of the first inner sleeve member and the front end of the second inner sleeve member can be avoided. Furthermore, this feature enables the operation of tampon extrusion to be reliably accomplished even though this operation is resisted by said interlocking effect to some extent. Said operation is further facilitated by providing the second inner sleeve member with the diameter-enlarged portion at the rear open end, since the diameter-enlarged portion advantageously offers a large area available for user's finger to bear thereagainst. Additionally, should said provisional interlocking between the first inner sleeve member and the second inner sleeve member be not reliably established when the tampon is not in use, the diameter-enlarged portion will prevent the second inner sleeve member from moving forward into the first inner sleeve member and eliminate anxiety for such movement.

The present invention thus provides a simple but extremely effective improvement in the applicator in which the inner sleeve comprises the first inner sleeve member and the second inner sleeve member.

SUMMARY OF THE INVENTION

The sanitary tampon applicator according to the present invention basically comprises a plastic outer sleeve to accommodate a tampon therein and a plastic inner sleeve slidably telescoped into said outer sleeve, said outer sleeve being provided adjacent its rear end with a first stopper directed radially inwards, said inner sleeve comprising a first inner sleeve member and a second inner sleeve member slidably inserted into said first inner sleeve member, said first inner sleeve member being provided at its front open end with a second stopper directed radially outwards so as to be engaged with said first stopper and at its rear open end with a third stopper directed radially inwards, said second inner sleeve member being provided at its front end with a fourth stopper and a fifth stopper both directed radially outwards, said fourth stopper being brought into engagement with said third stopper as said second inner sleeve member is pulled rearwards and said fifth stopper being so spaced axially behind said fourth stopper that said third stopper may be interposed between these both stoppers when said second inner sleeve member has been completely pulled rearwards.

Such construction is basically identical to that of the well known applicators.

The present invention is characterized, in this construction, by that said first inner sleeve member is provided at its front open end with a sixth stopper directed radially inwards to retain said second inner sleeve member against moving towards the axial direction of said first inner sleeve member; that said fifth stopper is stationarily provided with a height equal to or less than that of said fourth stopper and gradually slopes down rearwards; and that the rear open end of said second inner sleeve member includes a diameter-enlarged portion of which the diameter is at least larger than that of the rear open end of said first inner sleeve member.

The present invention is preferably embodied in such a manner that said second inner sleeve member is held against axial displacement by interposition of said sixth stopper between said fourth stopper and said fifth stopper unless said second inner sleeve member is pulled rearwards; that said fifth stopper opposed to said fourth stopper has its inner side substantially normal to the outer side of said second inner sleeve member; that said third stopper has a height substantially equal to that of said fourth stopper; that said fifth stopper has a height less than that of said fourth stopper; that there are provided at least a pair of said fifth stoppers opposed to each other; that said fourth stopper has a cutaway portion at a position opposed to said fifth stopper; that said first, second, third and sixth stoppers circumferentially extend around outer periphery of said sleeve members, respectively; and that said first inner sleeve member and said second inner sleeve member are made of synthetic resin harder than said outer sleeve, and these sleeves have a suitable resilience in a diametrical direction.

PREPARED EMBODIMENT OF THE INVENTION

The present invention will be described by way of embodiment in reference with the accompanying drawing.

Figure 1:
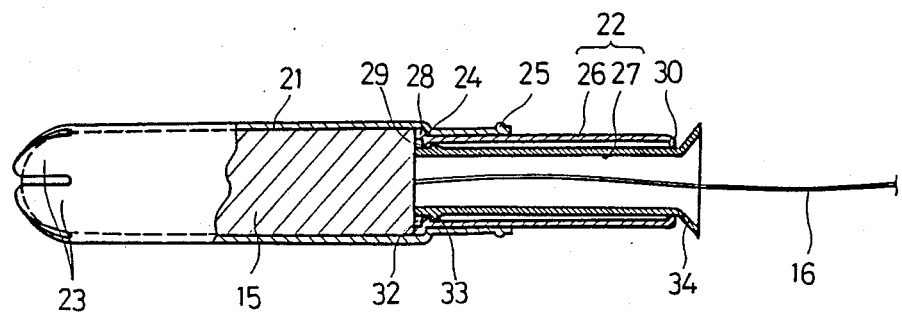
FIG. 1 is a fragmentary section view illustrating a tampon applicator according to the present invention as a first inner sleeve member and a second inner sleeve member constituting together an inner sleeve are not interlocked.
Figure 2:
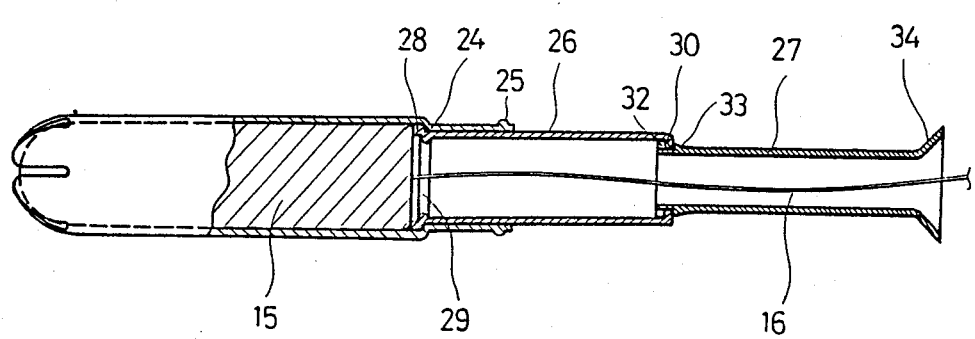
FIG. 2 is a view similar to FIG. 1 but illustrating the applicator as said sleeve members are interlocked.
Figure 3:
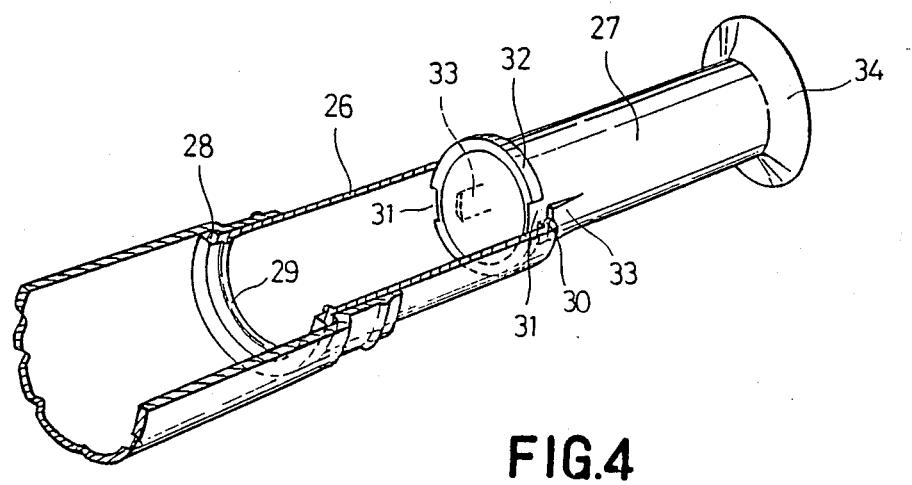
FIG. 3 is a partially broken perspective view illustrating the applicator as said sleeve members are interlocked.

As shown by FIGS. 1 through 3, the applicator constructed according to the present invention comprises a plastic outer sleeve 21 containing a tampon 15 previously inserted thereinto and a plastic inner sleeve 22 adapted to be slidably telescoped into the outer sleeve 21. These sleeves 21, 22 are molded of synthetic resin such as polyethylene and, therefore, have a suitable resilience in a diametrical direction.

Figure 12:
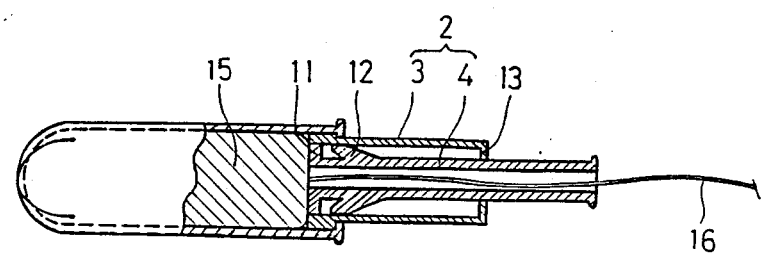
Figure 13:
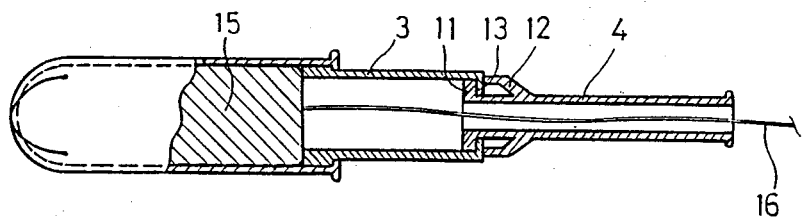

The outer sleeve 21 is closed at its front end by petal-like segments 23 integral with the outer sleeve 21 and the segments 23 are spread apart from one another as the tampon 15 is pushed forward by the inner sleeve 22. The outer sleeve 21 is diameter-reduced along a length adjacent its rear end so as to form an annular shoulder 24 adapted to be engaged with a corresponding portion of the inner sleeve 22 in a manner as will be described. The outer sleeve 21 is provided at its rear open end with an annular rib 25 circumferentially extending around outer periphery thereof. The outer sleeve 21 may be held along the diameter-reduced portion extending from said shoulder 24 to said rib 25 between user's fingers when the tampon 15 is actually used. It should be understood that the outer sleeve 21 may have no diameter-reduced portion adjacent its rear open end in some cases, as seen from FIG. 12.

Figure 4:
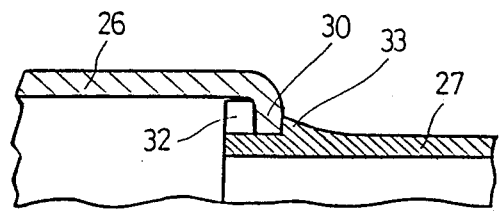
FIG. 4 is a fragmentary section illustrating the portions of the applicator interlocked, in an enlarged scale.
Figure 5:
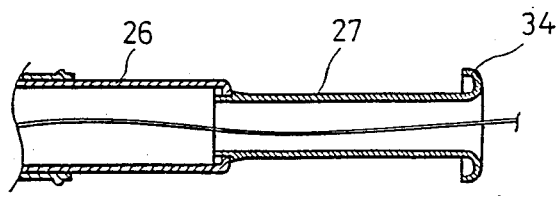
FIG. 5 is a sectional view illustrating another configuration of a diameter-enlarged portion at the rear open end of the second inner sleeve member.

The inner sleeve 22 comprises a first inner sleeve member 26 and a second inner sleeve member 27 slidably telescoped into said first inner sleeve member 26. The first inner sleeve member 26 is provided at its front open end with an annular projection 28 directed radially outwards so as to be engaged with the shoulder 24 of the outer sleeve 21 and thereby to prevent the first inner sleeve member 26 from falling out from the outer sleeve 21. The first inner sleeve member 26 is further provided at its front open end with a rib 29 circumferentially extending along inner periphery thereof for a purpose of provisional locking and at its rear open end with an annular projection 30 directed radially inwards. The second inner sleeve member 27 is provided at its front open end with a pair of arc-shaped ridges 32 circumferentially extending around outer periphery thereof and separated from each other by a pair of cutaway portions 31 diametrically opposed to each other and with a pair of stationary (foxed) projections 33 diametrically opposed to each other, with spacing behind said arc-shaped ridges 32. Each of these stationary projections 33 presents a shape of in equilateral triangle in cross-section, of which the inner side is vertical or slightly concave (see FIGS. 3 and 4). Provision of said cutaway portions 31 and the projections 33 facilitates it to remove the second inner sleeve member 27 from the die after having been molded. As seen from FIG. 4, the ridge 32 has a height substantially equal to that of the projection 30, but the projection 33 has a height smaller than that of the ridge 32 and gradually slopes down rearwards so that the projection 33 may ride across the projection 30 as the second inner sleeve member 27 is pulled rearwards. Said spacing between the ridges 32 and the projections 33 is so dimensioned that the rib 29 or the projection 30 may be interposed therebetween. The second inner sleeve member 27 is provided at its rear open end with a trumpet- or hopper-shaped diameter-enlarged portion 34. The diameter-enlarged portion 34 has a diameter at least larger than that of the first inner sleeve member 26 at its rear open end, preferably equal to or slightly larger than the diameter of the outer sleeve 21 at its rear open end. The diameter-enlarged portion 34 is molded by pressing the rear open end of the second inner sleeve member 27 against a heated die after said second inner sleeve member 27 has been inserted from the front open ahead of the first inner sleeve member 26 into it. It should be understood that the diameter-enlarged portion 34 may have a shape as shown by FIG. 5.

It is desired to alleviate uncomfortably rigid touch of the outer sleeve 21 for vagina, on one hand, and to assure reliable interlocking between the first inner sleeve member 26 and the second inner sleeve member 27 constituting together the inner sleeve 22, on the other hand. In view of such requirements, it is preferred that the former is made of relatively soft synthetic resin while the latter is made of relatively hard synthetic resin, although this is not essential to the present invention.

Figure 6:
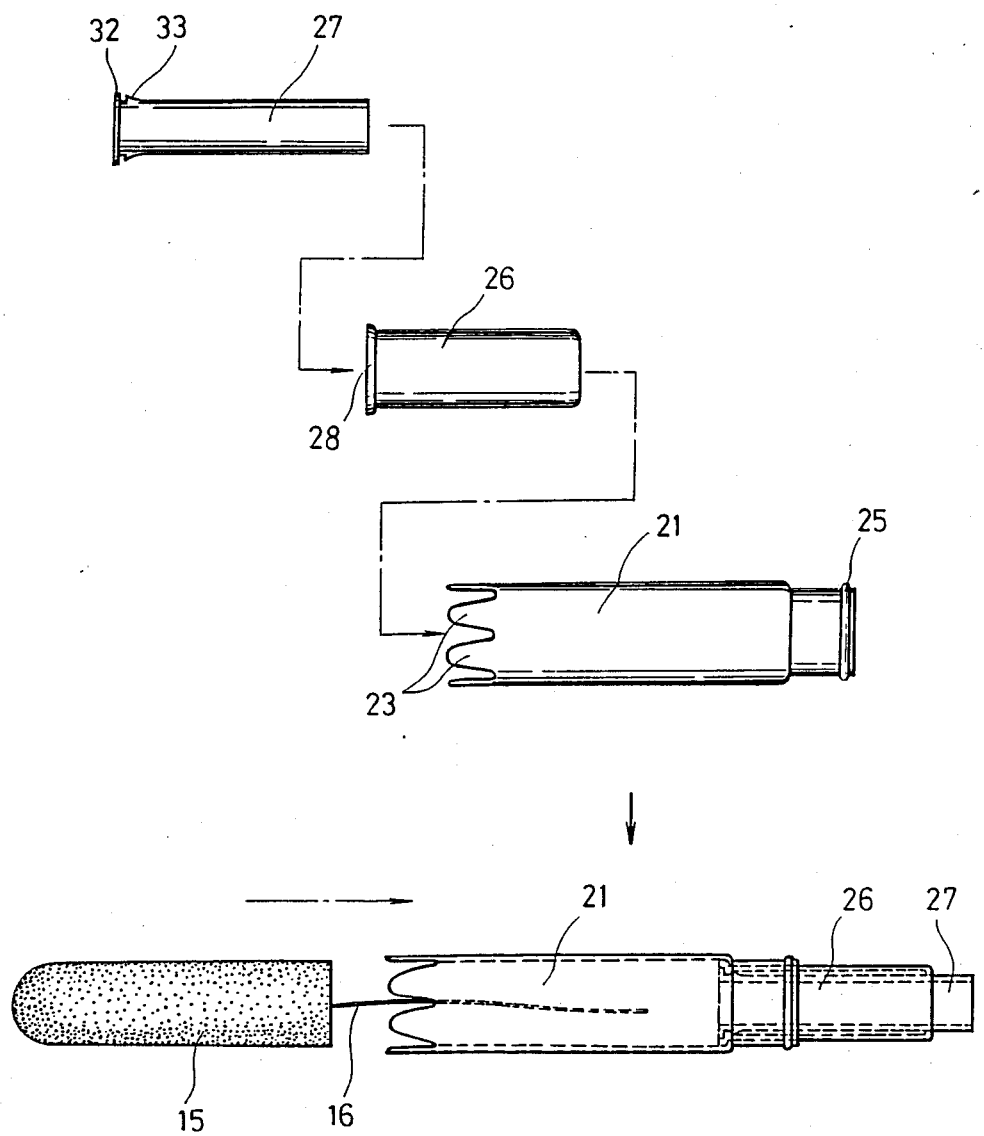
FIG. 6 is a side view illustrating the assembly steps of a tampon, the first inner sleeve member and the second inner sleeve member.

The sanitary tampon provided with the applicator of the construction as has been described hereinabove may be manufactured through steps as illustrated by FIG. 6. More specifically, the tampon 15 including the pull-chord 16 is shaped from fibrous material such as cotton, rayon, polypropylene and polyester while the outer sleeve 21, the first inner sleeve member 26 and the second inner sleeve member 27 are molded from thermoplastic synthetic resin such as polyethylene, in said configuration and construction by the shaping and molding methods of well known art, respectively. Then the first inner sleeve member 26 is inserted into the outer sleeve 21 and thereafter the second inner sleeve member 27 is inserted into the first inner sleeve member 26 or the first inner sleeve member 26 into which the second inner sleeve member 27 has previously been inserted is inserted together into the outer sleeve 21. Subsequently, the tampon 15 is inserted into the outer sleeve 21 with the pull-chord 16 being guided through the second inner sleeve member 27 and let out through the rear open end thereof. Then, the petal-like segments 23 are so bent under heating by the well known molding process to close the front open end of the outer sleeve 21.

Figure 7:
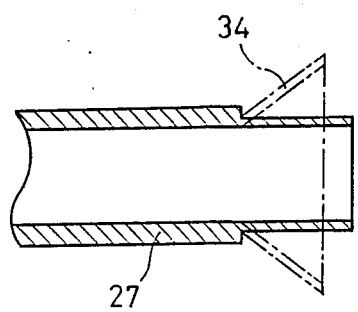
FIG. 7 is a sectional view illustrating further configuration of the diameter-enlarged portion at the rear open end of the second inner sleeve member.
Figure 8:
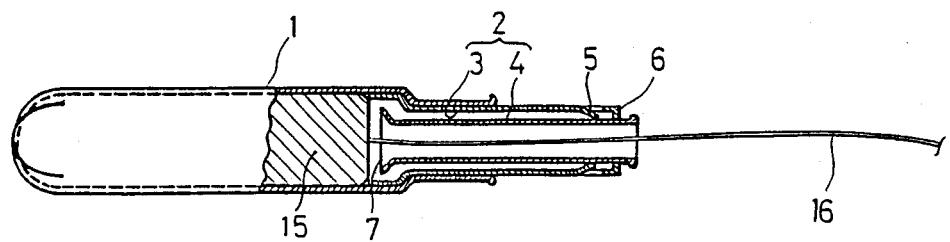
Figure 9:
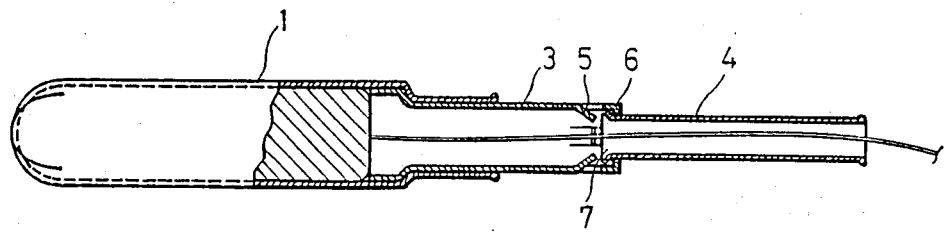
Figure 10:
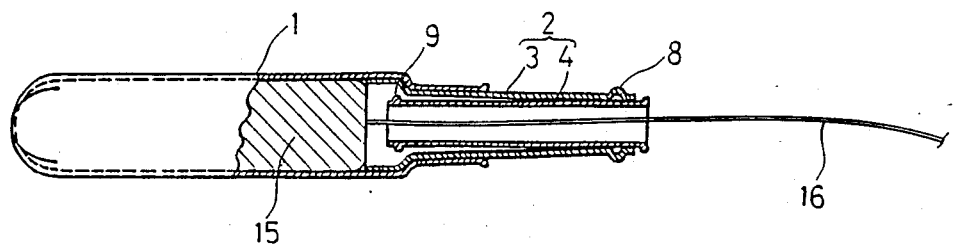
Figure 11:
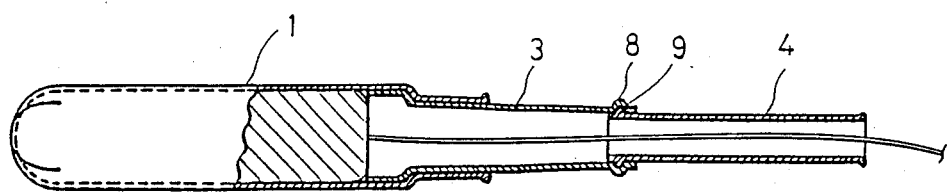

Simultaneously, or before or after the front open end of the outer sleeve 21 is closed, the rear open end of the second inner sleeve member 27 projecting from the rear open end of the first inner sleeve member 26 is bent outwards by the heating die to form the diameter-enlarged portion 34. Formation of the portion 34 in a relatively small thickness as illustrated by FIG. 7 permits an extent of bending by pressing said rear open end of the second inner sleeve member 27 against the heating die to be visually observed and thereby significantly facilitates this molding process.

With the applicator having such construction as has been described hereinabove, when the tampon 15 is still not in use, the second inner sleeve member 27 lies within the first inner sleeve member 26 with the rib 29 being interposed between the ridges 32 and the projections 33, as seen from FIG. 1, so that the second inner sleeve member 27 is locked against axial displacement. However, such locking of the member 27 is only provisional measure in order to prevent the second inner sleeve member 27 from axial displacement within the first inner sleeve member 26 during non-use of the tampon. Specifically, the ridge 32 rather easily rides across the rib 29 as the second inner sleeve member 27 is pulled rearwards in use of the tampon, since the rib 29 is dimensioned in the minimum height to achieve said provisional locking effect, preferably in the shape of circular arc and both the first inner sleeve member 26 and the second inner sleeve member 27 have a suitable resilience, although these members are made of relatively hard synthetic resin. When the second inner sleeve member 27 thus released to be axially slidable is further pulled rearwards, the projections 33 ride across the projection 30 which comes, in turn, between the ridges 32 and the projections 33, as seen from FIGS. 2 through 4. The reason for which the projections 33 can ride across the projection 30 in spite of being stationary will be readily understood from the reason for which the ridges 32 can ride across the rib 29.

What is claimed is:

1. A sanitary tampon applicator basically comprising a plastic outer sleeve to accommodate a tampon and a plastic inner sleeve slidably telescoped into said outer sleeve to extrude said tampon through a front open end of said outer sleeve, said outer sleeve being provided adjacent its rear end with a first stopper directed radially inwards, said inner sleeve comprising a first inner sleeve member and a second inner sleeve member slidably inserted into said first inner sleeve member, said first inner sleeve member being provided at its front open end with a second stopper directed radially outwards so as to be engaged with said first stopper and at its rear open end with a third stopper directed radially inwards, said second inner sleeve member being provided at its front open end with a fourth stopper and a fifth stopper both directed radially outwards, said fourth stopper being brought into engagement with said third stopper as said second inner sleeve member is pulled rearwards and said fifth stopper being so spaced axially behind said fourth stopper that said third stopper may be interposed between these both stoppers when said second inner sleeve member has been completely pulled rearwards, characterized by that said first inner sleeve member is provided at its front open end with a sixth stopper directed radially inwards to retain said second inner sleeve member against moving towards the axial direction of said first inner sleeve member; that said fifth stopper is stationarily provided with a height equal to or less than that of said fourth stopper and gradually slopes down rearwards; and that the rear open end of said second inner sleeve member includes a diameter-enlarged portion of which the diameter is at least larger than that of the rear open end of said first inner sleeve member.

2. An applicator as defined by claim 1, wherein said second inner sleeve member is held against axial displacement by interposition of said sixth stopper between said fourth stopper and said fifth stopper unless said second inner sleeve member is pulled rearwards.

3. An applicator as defined by claim 2, wherein said fifth stopper opposed to said fourth stopper has its inner side substantially normal to the outer side of said second inner sleeve member.

4. An applicator as defined by claim 1, wherein said third stopper has a height substantially equal to that of said fourth stopper.

5. An applicator as defined by claim 1, wherein said fifth stopper has a height less than that of said fourth stopper.

6. An applicator as defined by claim 1, wherein there are provided at least a pair of said fifth stoppers opposed to each other.

7. An applicator as defined by claim 1, wherein said fourth stopper has a cutaway portion at a position opposed to said fifth stopper.

8. An applicator as defined by claim 1, wherein said first, second, third and sixth stoppers circumferentially extend around outer periphery of said sleeve members, respectively.

9. An applicator as defined by claim 1, wherein said first inner sleeve member and said second inner sleeve member are made of synthetic resin harder than said outer sleeve, and these sleeves have a suitable resilience in a diametrical direction.

* * * * *